US012669502B2

(12) United States Patent
Hong et al.

(10) Patent No.: US 12,669,502 B2
(45) Date of Patent: Jun. 30, 2026

(54) METHOD FOR MEMORY B CELL-SPECIFIC DIFFERENTIATION INDUCTION, AND USES THEREOF

(71) Applicant: KOREA RESEARCH INSTITUTE OF BIOSCIENCE AND BIOTECHNOLOGY, Daejeon (KR)

(72) Inventors: Jung Joo Hong, Daejeon (KR); Green Kim, Daejeon (KR); Hanseul Oh, Daejeon (KR); Bon Sang Koo, Daejeon (KR); Seung Ho Baek, Daejeon (KR); Phil Yong Kang, Daejeon (KR); Eun Ha Hwang, Daejeon (KR)

(73) Assignee: KOREA RESEARCH INSTITUTE OF BIOSCIENCE AND BIOTECHNOLOGY, Daejeon (KR)

( * ) Notice: Subject to any disclaimer, the term of this patent is extended or adjusted under 35 U.S.C. 154(b) by 942 days.

(21) Appl. No.: 17/871,775

(22) Filed: Jul. 22, 2022

(65) Prior Publication Data

US 2022/0357325 A1     Nov. 10, 2022

Related U.S. Application Data

(63) Continuation of application No. PCT/KR2021/000928, filed on Jan. 22, 2021.

(30) Foreign Application Priority Data

Jan. 22, 2020    (KR) ........................ 10-2020-0008914

(51) Int. Cl.
*G01N 33/569*         (2006.01)
*C12N 5/0781*         (2010.01)

(52) U.S. Cl.
CPC ..... *G01N 33/56972* (2013.01); *C12N 5/0635* (2013.01); *G01N 33/56966* (2013.01); *C12N 2506/11* (2013.01)

(58) Field of Classification Search
CPC ................... G01N 33/56966; G01N 33/56972
See application file for complete search history.

(56) References Cited

U.S. PATENT DOCUMENTS

| | | | |
|---|---|---|---|
| 5,817,516 A | 10/1998 | Kehry et al. | |
| 2003/0124122 A1 | 7/2003 | Berenson et al. | |

(Continued)

FOREIGN PATENT DOCUMENTS

| | | |
|---|---|---|
| CN | 106793780 A | 5/2017 |
| WO | 2018/013897 A1 | 1/2018 |

OTHER PUBLICATIONS

Ingvarsson et al. Stimulation of Human Peripheral Lymphocytes via CD3 and Soluble Antigen Abrogates Specific Antibody Production by Reducing Memory B Cell Nos. Scand. J. Immunol. 42: 331-336 (1995).*

(Continued)

*Primary Examiner* — Gailene Gabel
(74) *Attorney, Agent, or Firm* — Hauptman Ham, LLP

(57) ABSTRACT

The present invention relates to a method for memory B cell-specific differentiation induction and to uses thereof and, more specifically, to an anti-CD3 antibody or ligand in a biological sample obtained from and individual, a method for memory B cell-specific differentiation induction comprising a step of treating an anti-CD28 antibody or ligand, and a method for detection a memory B cell which is specific to a specific antigen by using same.

10 Claims, 7 Drawing Sheets

(56) References Cited

U.S. PATENT DOCUMENTS

| | | |
|---|---|---|
| 2006/0057123 A1 | 3/2006 | Ettinger et al. |
| 2016/0046907 A1 | 2/2016 | Young |
| 2016/0046908 A1 | 2/2016 | Xu et al. |
| 2017/0252429 A1* | 9/2017 | Robinson ............. C12N 5/0637 |

OTHER PUBLICATIONS

Crotty et al. Tracking human antigen-specific memory B cells: a sensitive and generalized ELISPOT system. Journal of Immunological Methods 286: 111-122 (2004).*

Aleksandra Jasiulewicz et al., "Homeostatic 'bystander' proliferation of human peripheral blood B cells in response to polyclonal T-cell stimulation in vitro," International Immunology, May 20, 2015, pp. 579-588, vol. 27. No. 11. 10 pages.

Caroline Johnson-Léger et al., "CD28 co-stimulation stabilizes the expression of the CD40 ligand on T cells," International Immunology, Aug. 1998, pp. 1083-1091, vol. 10, No. 8, 9 pages.

V Kindler et al., "Memory, but not naive, peripheral blood B lymphocytes differentiate into Ig-secreting cells after CD40 ligation and costimulation with IL-4 and the differentiation factors IL-2, IL-10, and IL-3," The Journal of Immunology, Sep. 1, 1997, pp. 2085-2090, vol. 159, No. 5, 7 pages.

Antonio Lanzavecchia, "Activation of human B lymphocytes: frequency of antigen-specific B cells triggered by alloreactive or by antigen-specific T cell clones," Eur. J. Immunol., Sep. 1983, pp. 733-738, vol. 13, No. 9, 6 pages.

Office Action dated Jan. 22, 2025 for corresponding Japanese Patent Application No. 2022-544675, along with an English translation (9 pages).

Stephen J. Klaus et al., "Costimulation through CD28 enhances T cell-dependent B cell activation via CD40-CD40L interaction", The Journal of Immunology, 1994, vol. 152, No. 12, pp. 5643-5652, cited in NPL No. 1.

Shane Crotty et al., "Tracking human antegen-specific memory B cells: a sensitive and generalized ELISPOT system", Journal of Immunological Methods, 2004, vol. 286, pp. 111-122, cited in NPL No. 1.

International Search Report issued on Apr. 28, 2021, in connection with International Patent Application No. PCT/KR2021/000928; along with English machine translation.

Written Opinion issued issued on Apr. 28, 2021, in connection with International Patent Application No. PCT/KR2021/000928.

Karahan et al., "Polyclonal B cell activation for accurate analysis of pre-existing antigen-specific memory B cells," Clinical and Experimental Immunology, 2014, vol. 177, pp. 333-340; cited in NPL Nos. 1 and 2.

* cited by examiner a: PBMC
b: PBMC from which CD4+ T cell has been removed
c: PBMC from which CD8+ T cell has been removed Regulatory cell/IgG removed blood

FIG. 5

METHOD FOR MEMORY B CELL-SPECIFIC DIFFERENTIATION INDUCTION, AND USES THEREOF

CROSS-REFERENCE TO RELATED APPLICATIONS

The present application is a Continuation of PCT application number PCT/KR2021/000928 filed on Jan. 22, 2021, which is based on and claims priority to Korean Patent Application No. 10-2020-0008914 filed on Jan. 22, 2020, in the Korean Intellectual Property Office, which are incorporated herein by reference in their entireties.

TECHNICAL FIELD

The present invention relates to a method for specifically inducing differentiation of memory B cells and uses thereof, and more particularly, to a method for specifically inducing differentiation of memory B cells comprising treating an anti-CD3 antibody or ligand; and an anti-CD28 antibody or ligand in a biological sample obtained from a subject, and a method for detecting memory B cells specific to a specific antigen using the same.

BACKGROUND ART

Our body has an immune memory process for pathogens or antigens when our body is attacked by pathogens such as viruses or bacteria, or experiences antigens of components that are not present in our body, such as vaccines. The immune memory process is referred to as a memory response, but due to the memory formed in our body, when our body is re-exposed to pathogens or vaccine antigens, a relevant immune response occurs larger and faster. Crucial immune cells leading this immune memory response are B and T cells, which play important roles in acquired immunity. Accordingly, if these immune cells are well isolated and analyzed, the quantity and quality of the immune memory of each human can be measured to not only become a criterion for determine what kind of immune situation our body has in the past, but also predict what kind of immune defense mechanism will work in the event of an invasion of pathogens in the future.

However, in clinical practice, due to complex and difficult limitations of cell diagnostic technology, most medical staffs do not easily enjoy advanced immune information for each patient. Currently, the most commonly used method is an indirect method of measuring and determining an antibody, which is considered a product of immune memory cell activity, in blood. However, such a conventional method has a disadvantage in that the maintenance degree of the antibody response varies depending on a type of pathogen and a host, and it is difficult to be used in a specific period of a disease in which the antibody is not formed.

A method of directly measuring immune memory cells also has large limitations, and the biggest reason is that the cells responsible for the immune memory exist in a very small number in the body. In addition, since most cells are present in immune organs (spleen, lymph node, and intestine) rather than blood useful for diagnosis, invasive sample acquisition technology or preparation process is complicated and the use of indirect imaging medical technology is required.

Meanwhile, according to the Clinical and experimental immunology 177:333-340, a method of treating various differentiation factor cocktails for the analysis of antigen-specific memory B cells is known. However, such a method has a limitation in that a differentiation into naive B cells that have not been exposed to antigens is induced to exhibit a non-specific antigen-antibody response.

Therefore, by avoiding invasive methods that require access to immune organs, etc., and using the most easily obtainable blood, only memory B cells are very accurately specifically differentiated, and as a result, there is a need for a method capable of confirming whether there are memory B cells specific to a specific antigen.

DISCLOSURE

Technical Problem

Therefore, the present inventors had made many researches to develop a method capable of specifically inducing differentiation of only memory B cells using blood that may be obtained by a non-invasive method, and as a result, found that the differentiation of only the memory B cells may be specifically induced by treating an anti-CD3 antibody or ligand; and an anti-CD28 antibody or ligand in a biological sample obtained from a subject, and then completed the present invention.

An object of the present invention is to provide a method for specifically inducing differentiation of memory B cells comprising treating an anti-CD3 antibody or ligand; and an anti-CD28 antibody or ligand in a biological sample obtained from a subject.

Another object of the present invention is to provide a method for detecting antigen-specific memory B cells comprising (a) treating an anti-CD3 antibody or ligand; and an anti-CD28 antibody or ligand in a biological sample obtained from a subject; (b) treating an antigen in the biological sample; and (c) detecting an antibody specifically binding to the antigen.

Yet another object of the present invention is to provide a composition for specifically inducing differentiation of memory B cells comprising an anti-CD3 antibody or ligand; and an anti-CD28 antibody or ligand.

Still another object of the present invention is to provide a composition for specifically inducing differentiation of memory B cells consisting of an anti-CD3 antibody or ligand; and an anti-CD28 antibody or ligand.

Still another object of the present invention is to provide a composition for specifically inducing differentiation of memory B cells essentially consisting of an anti-CD3 antibody or ligand; and an anti-CD28 antibody or ligand.

Still yet another object of the present invention is to provide uses of an anti-CD3 antibody or ligand; and an anti-CD28 antibody or ligand for preparing an agent for specifically inducing differentiation of memory B cells.

Technical Solution

According to an aspect of the present invention, there is provided a method for specifically inducing differentiation of memory B cells comprising treating an anti-CD3 antibody or ligand; and an anti-CD28 antibody or ligand in a biological sample obtained from a subject.

According to another aspect of the present invention, there is provided a method for detecting antigen-specific memory B cells comprising (a) treating an anti-CD3 antibody or ligand; and an anti-CD28 antibody or ligand in a biological sample obtained from a subject; (b) treating an antigen in the biological sample; and (c) detecting an antibody specifically binding to the antigen.

According to yet another aspect of the present invention, there is provided a composition for specifically inducing differentiation of memory B cells comprising an anti-CD3 antibody or ligand; and an anti-CD28 antibody or ligand.

According to yet another aspect of the present invention, there is provided a composition for specifically inducing differentiation of memory B cells consisting of an anti-CD3 antibody or ligand; and an anti-CD28 antibody or ligand.

According to yet another aspect of the present invention, there is provided a composition for specifically inducing differentiation of memory B cells essentially consisting of an anti-CD3 antibody or ligand; and an anti-CD28 antibody or ligand.

According to still another aspect of the present invention, there is provided uses of an anti-CD3 antibody or ligand; and an anti-CD28 antibody or ligand for preparing an agent for specifically inducing differentiation of memory B cells.

Hereinafter, the present invention will be described in detail.

According to an exemplary embodiment of the present invention, it was confirmed that when an anti-CD3 antibody or ligand; and an anti-CD28 antibody or ligand were treated in PBMC derived from a blood obtained from a subject, memory B cell-specific differentiation was induced, while differentiation of naive B cells was not induced.

Accordingly, the present invention provides a method for specifically inducing differentiation of memory B cells comprising treating an anti-CD3 antibody or ligand; and an anti-CD28 antibody or ligand in a biological sample obtained from a subject.

In the present invention, the "subject" is not particularly limited to its type, but may be, for example, a human, a monkey, a dog, a cat, a rabbit, a guinea pig, a rat, a mouse, a cow, a sheep, a pig or a goat, preferably a human.

In particular, the subject may be a subject to analyze whether there is a history of infection with bacteria or viruses in the past.

In the present invention, the "biological sample" is not particularly limited to its type so long as the biological sample is samples obtained from the subject. For example, the biological sample may be selected from the group consisting of whole blood, plasma, serum, peripheral blood mononuclear cells (PBMC), urine, feces, saliva, sputum, sweat, tears, tissues and combinations thereof, preferably, whole blood, plasma, serum, PBMC and combinations thereof, and most preferably PBMC.

In the present invention, the "anti-CD3 antibody" or "anti-CD28 antibody" refers to a specific protein molecule indicated against an antigenic region of CD3 or CD28 expressed on the surface of CD4$^+$ T cells. For the purposes of the present invention, the antibody refers to an antibody that specifically binds to CD3 or CD28 to activate the CD4$^+$ T cells, and includes all polyclonal antibodies, monoclonal antibodies, and recombinant antibodies.

The antibody of the present invention includes a functional fragment of the antibody molecule as well as a complete form having two full-length light chains and two full-length heavy chains. The functional fragment of the antibody molecule refers to a fragment having at least an antigen binding function, and includes Fab, F(ab'), F(ab') 2, Fv and the like, but is not limited thereto.

In the present invention, the "ligand" refers to all kinds of molecules capable of binding to CD3 or CD28. Preferably, the ligand refers to all kinds of molecules that bind to CD3 or CD28 to activate CD4$^+$ T cells.

In the present invention, the "T cells" refer to T lymphocytes as defined in the art and may include thymocytes, immature T lymphocytes, mature T lymphocytes, resting T lymphocytes, or activated T lymphocytes.

In the present invention, the term "CD4$^+$ T cells" refers to subsets of T cells that express CD4 on the surfaces thereof and are associated with cell-mediated immune responses. The CD4$^+$ T cells are characterized by a secretion profile after stimulation, which may include secretion of cytokines such as IFN-gamma, TNF-alpha, IL-2, IL-4 and IL-10.

In the present invention, the term "specific" refers to inducing differentiation of only memory B cells among various immune cells, particularly naive B cells and memory B cells, present in the biological sample.

In the present invention, the term "memory B cell" is used interchangeably with a memory B cell, and is one of B cell subtypes formed in germinal centers after primary infection. The memory B cells accelerate the immune response and generate a robust antibody-mediated immune response when secondarily infected with the same pathogen.

In the present invention, the "naive B cell" refers to a B cell that has never been exposed to an antigen. When the naive B cells are exposed to the antigen, the naive B cells are differentiated into memory B cells and antibody-secreting plasma cells.

In the present invention, the "specifically inducing the differentiation of the memory B cells" refers to converting memory B cells that do not secrete an antibody into plasma cells that secrete an antibody against a specific antigen. When the memory B cells are differentiated into plasma cells, the memory B cells express IgG and IgM in response to a specific antigen programmed into their respective memories.

Meanwhile, according to an exemplary embodiment of the present invention, it was confirmed that when a step of removing CD8$^+$ T cells from the biological sample is further performed before treating the anti-CD3 antibody or ligand; and the anti-CD28 antibody or ligand in the biological sample, the differentiation of memory B cells was significantly improved.

Accordingly, the method provided by the present invention may be characterized by further comprising a step of removing CD8$^+$ T cells from the biological sample before treating the anti-CD3 antibody or ligand; and the anti-CD28 antibody or ligand in the biological sample obtained from the subject.

In the present invention, the term "CD8$^+$ T cells" refer to a subset of T cells that express CD8 on the surfaces thereof, are MHC class I-restricted, and act as cytotoxic T cells. The "CD8" molecule is a differentiation antigen found on thymocytes and on cytotoxic and inhibitory T-lymphocytes. The CD8 antigen is a member of an immunoglobulin supergene system and is an associative recognition element in major histocompatibility complex class I-restricted interactions.

In the present invention, the method for removing the CD8$^+$ T cells is not particularly limited, but may be removed by, for example, flow cytometry, fluorescence activated cell sorting (FACS), magnetic beads, columns, or the like. Antibodies or beads that respond to CD8 molecules on the cell surface are treated in the isolated PBMCs to selectively remove the corresponding cells using FACS or a column.

The present invention provides a method for detecting antigen-specific memory B cells comprising (a) treating an anti-CD3 antibody or ligand; and an anti-CD28 antibody or ligand in a biological sample obtained from a subject; (b) treating an antigen in the biological sample; and (c) detecting an antibody specifically binding to the antigen.

The method of the present invention relates to a method of detecting whether an antibody specifically recognizing a specific antigen is present among antibodies secreted by differentiated memory B cells using the aforementioned method for specifically inducing the differentiation of the memory B cells.

Since the memory B cells present in the biological sample obtained from the subject are formed after the subject has been exposed to the specific antigen in the past, in step (a), the memory B cells present in the biological sample are differentiated into plasma cells secreting the antibody and respond to the specific antigen, so that it can be confirmed whether the memory B cells for the specific antigen are present in the biological sample. That is, it is possible to establish a rapid treatment strategy by confirming whether the subject has been infected with bacteria or viruses containing the antigen in the past.

Step (a) may be understood in the same manner with reference to the description.

In the present invention, step (b) is a step of inducing an antigen-antibody response between an antibody secreted by the memory B cells differentiated into the plasma cells secreting the antibody in step (a) and an antigen of interest.

In step (b) of the present invention, the "antigen" is not particularly limited to its type as long as the antigen is expressed by pathogenic substances, more specifically, bacteria or viruses.

The antigen may include peptides, proteins, nucleic acids, sugars, pathogens, attenuated pathogens, inactivated pathogens, viruses, virus-like particles (VLPs), cells or cell fragments.

Non-limiting examples of the "antigen" may include a *Mycobacterium tuberculosis* antigen, an anthrax antigen, a Hepatitis A virus (HAV) antigen, a Hepatitis B virus (HBV) antigen, a Hepatitis C virus (HCV) antigen, a human immunodeficiency virus (HIV) antigen, an influenza virus antigen, a Herpes simplex virus (HSV) antigen, a *Haemophilus influenzae* type b (Hib) antigen, a *Neisseria meningitidis* antigen, a *Corynebacterium diphtheria* antigen, a *Bordetella pertussis* antigen, a *Clostridium tetani* antigen, a human papilloma virus (HPV) antigen, a Varicella virus antigen, an Enterococci antigen, a *Staphylococcus aureus* antigen, a *Klebsiella pneumonia* antigen, an *Acinetobacter baumannii* antigent, a *Pseudomonas aeruginosa* antigen, an *Enterobacter* antigen, a *Helicobacter pylori* antigen, a malaria antigen, a Dengue virus antigen, a MERS virus antigen, a Zika virus antigen, an Orientia tsutsugamushi antigen, a severe fever with thrombocytopenia syndrome Bunyavirus (SFTS Bunyavirus) antigen, a Japanese encephalitis virus antigen, a severe acute respiratory syndrome-corona virus (SARS-CoV) antigen, a severe acute respiratory syndrome-corona virus-2 (SARS-CoV-2) antigen, an Ebola virus antigen, a hepatitis C virus antigen, a hepatitis B virus antigen, an acute respiratory syndrome virus antigen, a West Nile virus antigen, a vesicular stomatitis virus antigen, a Newcastle disease virus antigen or a pneumococcal antigen.

Step (c) is a step of confirming whether the antigen treated in step (b) and the antibody secreted by the memory B cells induced to be differentiated from the biological sample cause an antigen-antibody response.

The method for detecting the antigen-antibody response in step (c) may be used without limitation as long as the method is a method known in the art, and non-limiting examples thereof may include ELISPOT, ELISA, competitive ELISA, magnetic beads or immunochromatography. Preferably, the method for detecting the antigen-antibody response may be ELISPOT.

When the antibody specifically binding to the antigen is detected in step (c), it may be determined that the subject has a history of infection with pathogenic substances expressing the antigen, more specifically, bacteria or viruses.

The present invention provides a composition for specifically inducing differentiation of memory B cells comprising an anti-CD3 antibody or ligand; and an anti-CD28 antibody or ligand.

The composition of the present invention may further include factors required for the survival of memory B cells in addition to the anti-CD3 antibody or ligand; and the anti-CD28 antibody or ligand. For example, the composition includes a suitable medium (i.e., Minimal,) Essential Media or RPMI Media 1640 or, X-vivo 5, (Lonza)), which may contain serum (i.e., fetal bovine or human serum), cytokines, or any other additives for the growth of cells known to those skilled in the art. Other additives for the growth of cells include a surfactant, plasmanate and a reducing agent such as N-acetyl-cysteine and 2-mercaptoethanol, but are not limited thereto. The media may include an optimizer, X-Vivo 20, sodium pyruvate and vitamins, serum-free, or appropriate amount of serum (or plasma)-supplemented, or hormones-defined sets, and/or a sufficient amount of cytokine(s) for growth and expansion of T-cells in addition to RPMI 1640, A1M-V, DMEM, MEM, a-MEM, F-12, X-Vivo 1, and added amino acids, but are not limited thereto.

The present invention provides uses of an anti-CD3 antibody or ligand; and an anti-CD28 antibody or ligand for preparing an agent for specifically inducing differentiation of memory B cells.

The term 'comprising' of the present invention is used in the same manner as 'containing' or 'characterizing', and does not exclude additional ingredients or steps of the method which are not mentioned in the composition or the method. The term 'consisting of' means excluding additional elements, steps or ingredients, etc., which are not separately described. The term 'essentially consisting of' means including ingredients or steps that do not substantially affect basic properties thereof in addition to the described ingredients or steps within the range of the composition or the method.

Advantageous Effects

According to the method of the present invention, since only memory B cells present in a biological sample may be specifically differentiated, it is possible to very accurately and quickly analyze whether a subject providing the biological sample has a history of infection with pathogenic substances containing a specific antigen.

DESCRIPTION OF DRAWINGS

FIG. 5 illustrates a result of confirming whether to secrete IgM and IgG using ELISPOT by treating (i) anti-CD3 and anti-CD8 antibodies (immunoreceptor activity treated group), (ii) a TLR7/8 agonist (R848) or (iii) a TLR9 agonist (CPG) after isolating PBMC from the blood of monkeys which has been exposed or not to an MERS antigen (immunoreceptor activity treated group: anti-CD3 antibody and anti-CD8 antibody treated group, TLR agonist 1: TLR7/8 agonist (R848), TLR agonist 2: TLR9 agonist (CPG)).

MODES FOR THE INVENTION

Hereinafter, the present invention will be described in detail by the following Examples. However, the following Examples are just illustrative of the present invention, and the contents of the present invention are not limited to the following Examples.

Example 1: Isolation of Peripheral Blood Mononuclear Cells (PBMCs)

The blood was isolated from a normal human and a non-human primate. The blood in an EDTA tube was mixed with 1×PBS, and then layers were slowly separated in 4 ml of Ficoll-Hypaque (Lymphoprep; Axis-Shield, 1114545). After centrifuging slowly at 4000 rpm for 20 minutes, when the layers were divided, white bands of PBMCs were collected using a pipette. The PBMCs were added with 1×PBS again and centrifuged at 1500 rpm for 5 minutes, and then a supernatant was removed. Thereafter, 1 ml of a medium was added to release the cells. The number of cells was counted using an Olympus R1 automatic cell counter.

Example 2: Induction of Differentiation of Memory B Cells by Treating Anti-CD3 Antibody or Ligand; and Anti-CD28 Antibody or Ligand (1) Measurement of Antibody Secretion Amount According to Treatment of Anti-CD3 Antibody or Ligand; and Anti-CD28 Antibody or Ligand to PBMC An anti-CD3 antibody or ligand; and an anti-CD28 antibody or ligand were treated to the PBMCs isolated in Example 1.

The PBMCs (1×10$^5$ cells/well) isolated in Example 1 were added to a 96-well plated coated with 1 ug/ml of an anti-CD3 antibody (Clone OKT3, Biolegend Cat. No. 317302), treated with 1 ug/ml of an anti-CD28 antibody (Clone CD28.2, BD Cat. No. 555725), and then reacted in a 37° C., 5% CO$_2$ incubator for 3 to 4 days.

Since the antibodies secreted from the memory B cells consisted of IgG and IgM types, the amounts of IgM and IgG secreted from the PBMC sample were then measured through an ELISPOT method.

Specifically, 10 ug/ml of anti-IgG and IgM antibodies were added into each plate by 50 ul, and then coated at 4° C. for 24 hours. The PBMCs stimulated with the anti-CD3 antibody and the anti-CD28 antibody were added to the coated plate, and then reacted in a 37° C., 5% CO$_2$ incubator for 4 hours. Thereafter, an anti-IgG-FITC antibody and an IgM-Biotin antibody (Southern Biotech) reacted at room temperature for 2 hours, and FITC-HRP and Strep-AP (CTL) reacted at room temperature for 1 hour. Finally, a blue reducing agent was added and then reacted at room temperature for 15 minutes, and then IgM and IgG were measured.

Figure 1:
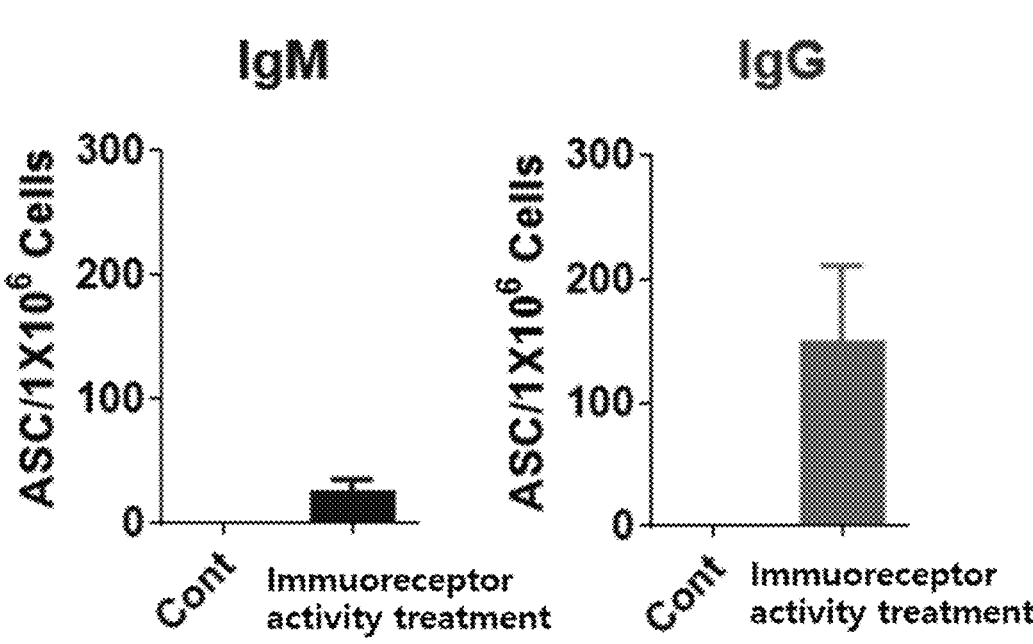
FIG. 1 illustrates a result of detecting IgM and IgG secreted using ELISPOT after treating isolated PBMC with anti-CD3 and anti-CD8 antibodies (immunoreceptor activity treated group: anti-CD3 antibody and anti-CD8 antibody treated group).

The result thereof was illustrated in FIG. 1.

As illustrated in FIG. 1, it was confirmed that when the anti-CD3 antibody or ligand; and the anti-CD28 antibody or ligand were treated to the PBMCs, the secretion amount of IgG and IgM-type antibodies significantly increased compared to PBMCs untreated with the anti-CD3 antibody or ligand; and the anti-CD28 antibody or ligand. That is, the differentiation of memory B cells was induced by treatment of the anti-CD3 antibody or ligand; and the anti-CD28 antibody or ligand, and as a result, it could be expected that the secretion of IgG and IgM from the differentiated B cells was increased.

(2) Induction of Differentiation of Memory B Cells in PBMCs from which CD4$^+$ T Cells or CD8$^+$ T Cells have been Removed In order to optimize conditions in which the differentiation of the memory B cells was induced when the anti-CD3 antibody or ligand; and the anti-CD28 antibody or ligand were treated in the experiment (1), CD4$^+$ T cells or CD8$^+$ T cells were removed from PBMCs and then the anti-CD3 antibody or ligand; and the anti-CD28 antibody or ligand were treated by the same method as the experiment.

The CD4$^+$ T cells or CD8$^+$ T cells were removed from the PBMCs by the following method, respectively.

Specifically, PBMC-CD4 T cells (PBMCs from which CD4$^+$ T cells were removed) and PBMC-CD8 T cells (PBMCs from which CD8$^+$ T cells were removed) were isolated using an anti-CD4 microbead kit and an anti-CD8 microbead kit (Miltenyi Biotech, Auburn, Calif.). PBMCs (1×10$^7$ cells) were added with 80 μl of a buffer (0.5% BSA and 2 mM EDTA in PBS), mixed well by adding 20 μl of CD4 microbeads or CD8 microbeads, mix well, and then reacted at 4° C. for 15 minutes. After the reaction was stopped and the PBMCs were centrifuged at 1500 rpm for 5 minutes, PBMC-CD4 T cells or PBMC-CD8 T cells not attached to a magnet were obtained using 10 ml of a buffer and an LS MACS column (Miltenyi Biotech, Auburn, Calif.), respectively.

Figure 2:
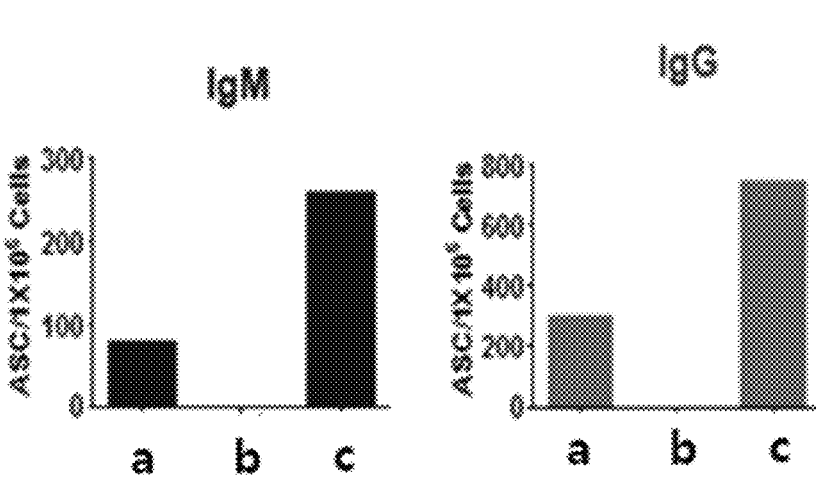
FIG. 2 illustrates a result of detecting secreted IgM and IgG using ELISPOT by removing CD4$^+$ T cells or CD8$^+$ T cells from isolated PBMC and then treating anti-CD3 and anti-CD8 antibodies.

The result thereof was illustrated in FIG. 2.

As illustrated in FIG. 2, it was confirmed that even if the PBMCs from which the CD4$^+$ T cells have been removed were treated with the anti-CD3 antibody or ligand; and the anti-CD28 antibody or ligand, the antibodies were not secreted at all. However, it was confirmed that as compared with PBMCs from which the CD8$^+$ T cells were removed, the secretion amount of antibodies was significantly increased by treatment with the anti-CD3 antibody or ligand; and the anti-CD28 antibody or ligand.

Therefore, the following experiment was performed using the PBMCs from which the CD8$^+$ T cells were removed.

(3) Confirmation of Whether Memory B Cell-Specific Differentiation has been Induced In the prior art, since substances treated to induce the differentiation of memory B cells were polycolonal activators, not only the memory B cells but also naive B cells were differentiated, so that it was impossible to specifically differentiate only B cells that actually have immune memory against a specific antigen.

Accordingly, the present inventors intended to confirm whether to specifically differentiate only memory B cells, not naive B cells by the method of treating the anti-CD3 antibody or ligand; and the anti-CD28 antibody or ligand to the PBMCs.

Specifically, the remaining cells from which cells expressing IgD and IgG were removed from the cell surface corresponding to the PBMCs were isolated using BD FACS Aria II. Thereafter, the isolated cells ($1 \times 10^5$ cells/well) were added to a 96-well plated coated with 1 ug/ml of an anti-CD3 antibody (Clone OKT3, Biolegend Cat. No. 317302) at the previous day, treated with 1 ug/ml of an anti-CD28 antibody (Clone CD28.2, BD Cat. No. 555725), and then reacted in a 37° C., 5% $CO_2$ incubator for 3 to 4 days, and thereafter, the antibody amounts were measured through the ELISPOT experiment.

Figure 3A:
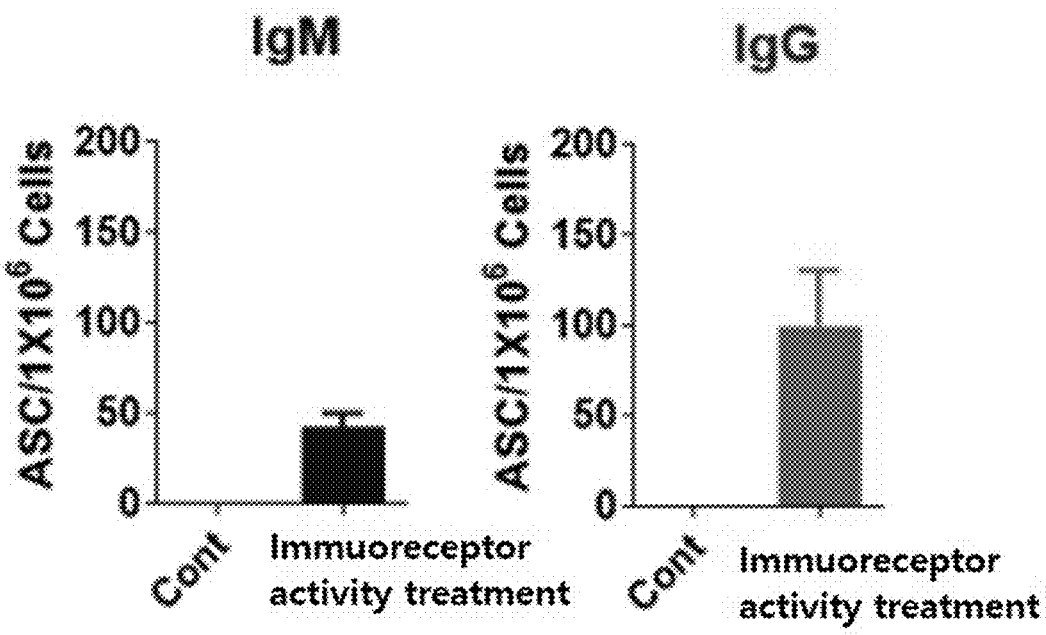
FIGS. 3A and 3B illustrate results of detecting secreted IgM and IgG using ELISPOT by removing IgD or IgG from PBMC from which CD8$^+$ T cells are removed and then treating anti-CD3 and anti-CD8 antibodies.
Figure 3B:
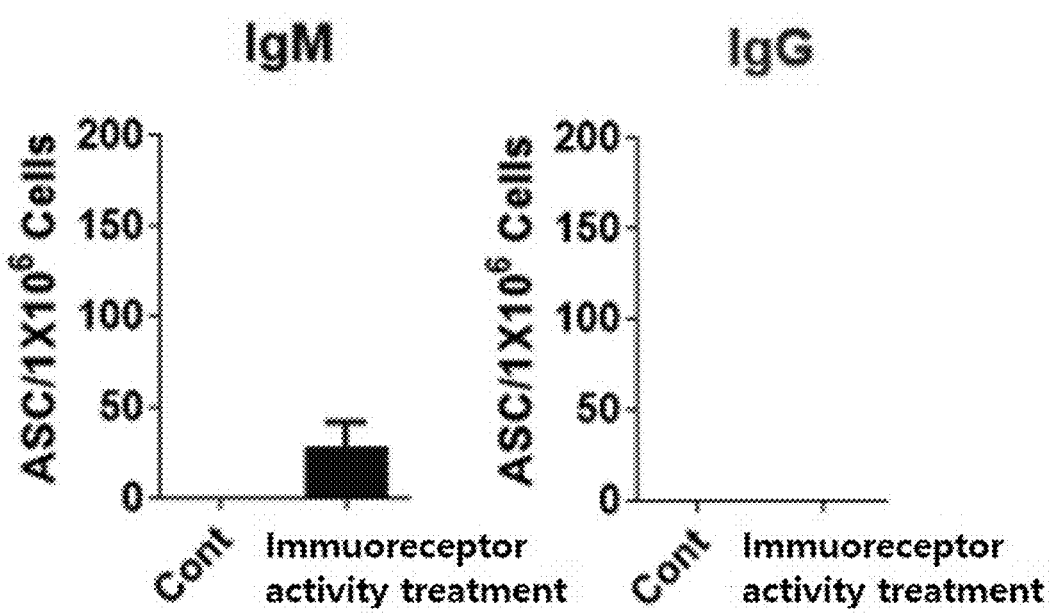

The results thereof were illustrated in FIGS. 3A and 3B.

As can be seen in FIG. 3A, it was confirmed that in PBMCs from which cells expressing IgD on the surface have been removed, the secretion amount of IgM and IgG-type antibodies was still increased by treatment with the anti-CD3 antibody or ligand; and the anti-CD28 antibody or ligand. In contrast, as can be seen in FIG. 3B, it was confirmed that in PBMCs from which cells expressing IgG on the surface were removed, even if the anti-CD3 antibody or ligand; and the anti-CD28 antibody or ligand were treated, the secretion of IgM and IgG-type antibodies was not increased at all.

That is, it can be seen that naive B cells expressing IgD on the surface were not differentiated into cells secreting the antibodies even if the anti-CD3 antibody or ligand; and the anti-CD28 antibody or ligand were treated, but the differentiation of only memory B cells expressing IgG on the surface has been induced by treatment of the anti-CD3 antibody or ligand; and the anti-CD28 antibody or ligand.

Polyclonal activators, substances used in previous studies, differentiate naive B cells that have not experienced the antigen to produce IgM antibodies on the surface that are not related to a memory of a specific antigen.

Therefore, the present inventors tried to confirm whether such a non-specific response existed by a method of treating PBMCs with TLR agonists, which were typically known as polyclonal activators.

Specifically, $IgD^+CD27^-$ cells expressing naive B cells were isolated from the cell surface corresponding to the PBMCs using BD FACS Aria II. Thereafter, the isolated cells ($1 \times 10^4$ cells/well) were added in a 96-well plate, treated with 1 ug/ml of TLR7/8 agonist (R848) and TLR9 agonist (CPG), and then reacted in a 37° C., 5% $CO_2$ incubator for 3 to 4 days, and thereafter, the antibody amount was measured through the ELISPOT experiment.

Figure 4:
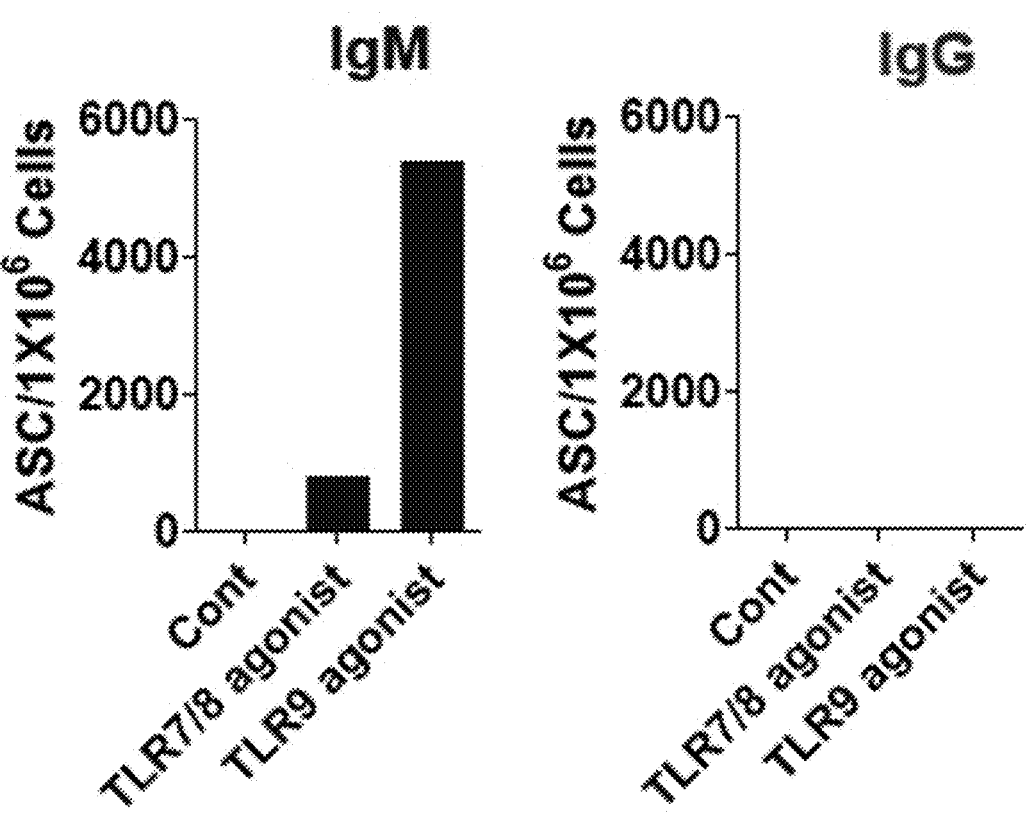
FIG. 4 illustrates a result of measuring the amount of antibodies through an ELISPOT experiment after isolating naive B cells from PBMC and treating polyclonal activators, TLR7/8 agonist (R848) and TLR9 agonist (CPG) at 1 ug/ml.
Figure 6A:
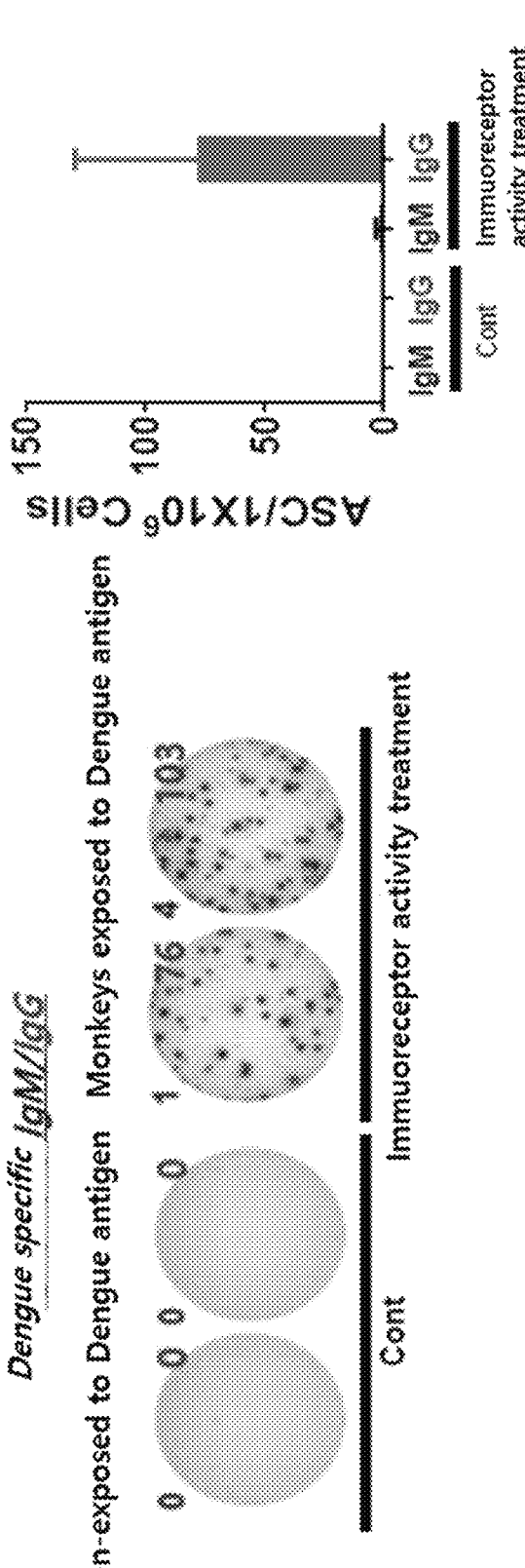
FIGS. 6A and 6B are results of confirming whether to secrete IgM and IgG using ELISPOT by treating anti-CD3 and anti-CD8 antibodies (immunoreceptor activity treated group) after isolating PBMC from the blood of monkeys which has been exposed or not to a Dengue virus antigen (FIG. 6A) or a COVID-19 virus antigen (FIG. 6B) and removing CD8$^+$ T cells (immunoreceptor activity treated group: anti-CD3 antibody and anti-CD8 antibody treated group).
Figure 6B:
Figure 6B:
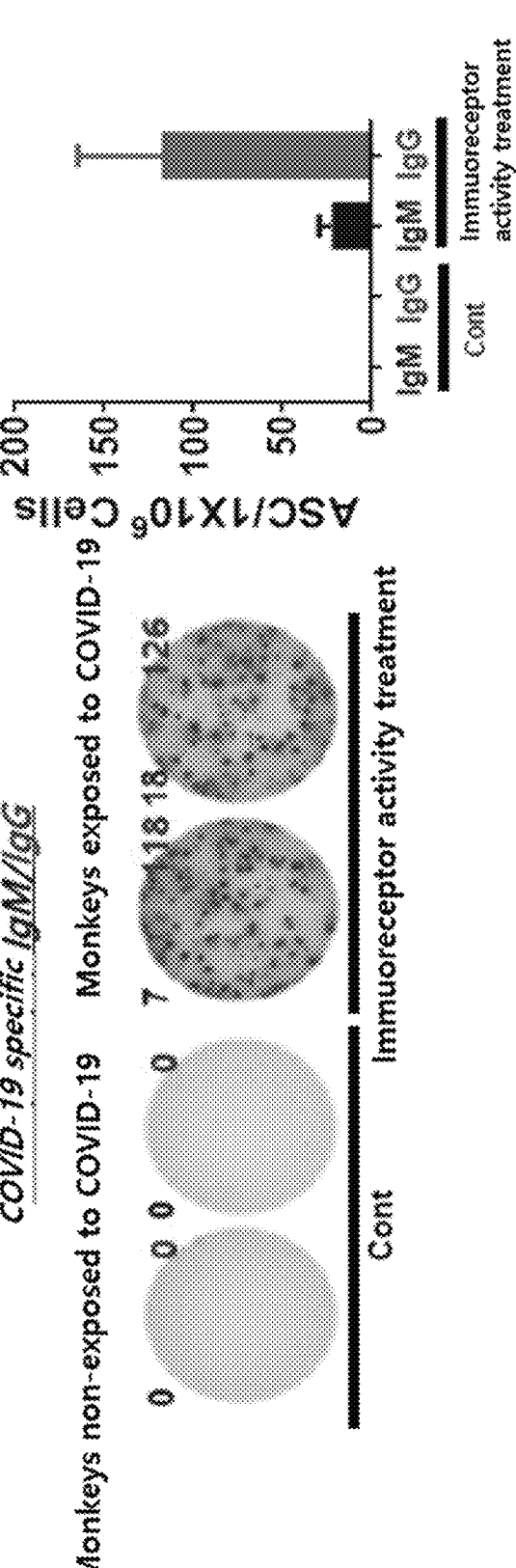

The result thereof was illustrated in FIG. 4.

As illustrated in FIG. 4, it was confirmed that the secretion amount of IgM was significantly increased in naive B cells treated with TLR7/8 agonist (R848) and TLR9 agonist (CPG). That is, it was found that the polyclonal activators induced differentiation of naive B cells that was not related to an antigen-specific memory.

Example 3: Detection of Memory B Cells Specific to Specific Antigen

After establishing a method for specifically differentiating only memory B cells in PBMCs through Examples 1 and 2, using the above method, it was evaluated to determine whether or not the memory B cells have been exposed to a specific antigen in a biological sample isolated from an actual subject.

Specifically, PBMCs of monkeys that had been tertiary-inoculated with MERS virus antigen protein and adjuvant in the thigh muscle were isolated. According to the method of the present invention, the isolated monkey PBMCs ($5 \times 10^5$ cells/well) were added to a 96-well plate coated with 1 ug/ml of an anti-CD3 antibody (Clone SP34, BD Cat. No. 557052) at the previous day, treated with 1 ug/ml of an anti-CD28 antibody (Clone CD28.2, BD Cat. No. 555725), and then reacted in a 37° C., 5% $CO_2$ incubator for 3 to 4 days. Alternatively, the isolated monkey PBMCs were treated with a polyclonal activator, TLR7/8 agonist (R848, TLR agonist1) or TLR9 agonist (CPG, TLR agonist 2) instead of the anti-CD3 antibody and the anti-CD28 antibody and then reacted in a 37° C., 5% $CO_2$ incubator for 3 to 4 days.

Thereafter, ELISPOT was performed by coating a MERS-specific protein.

Figure 5:
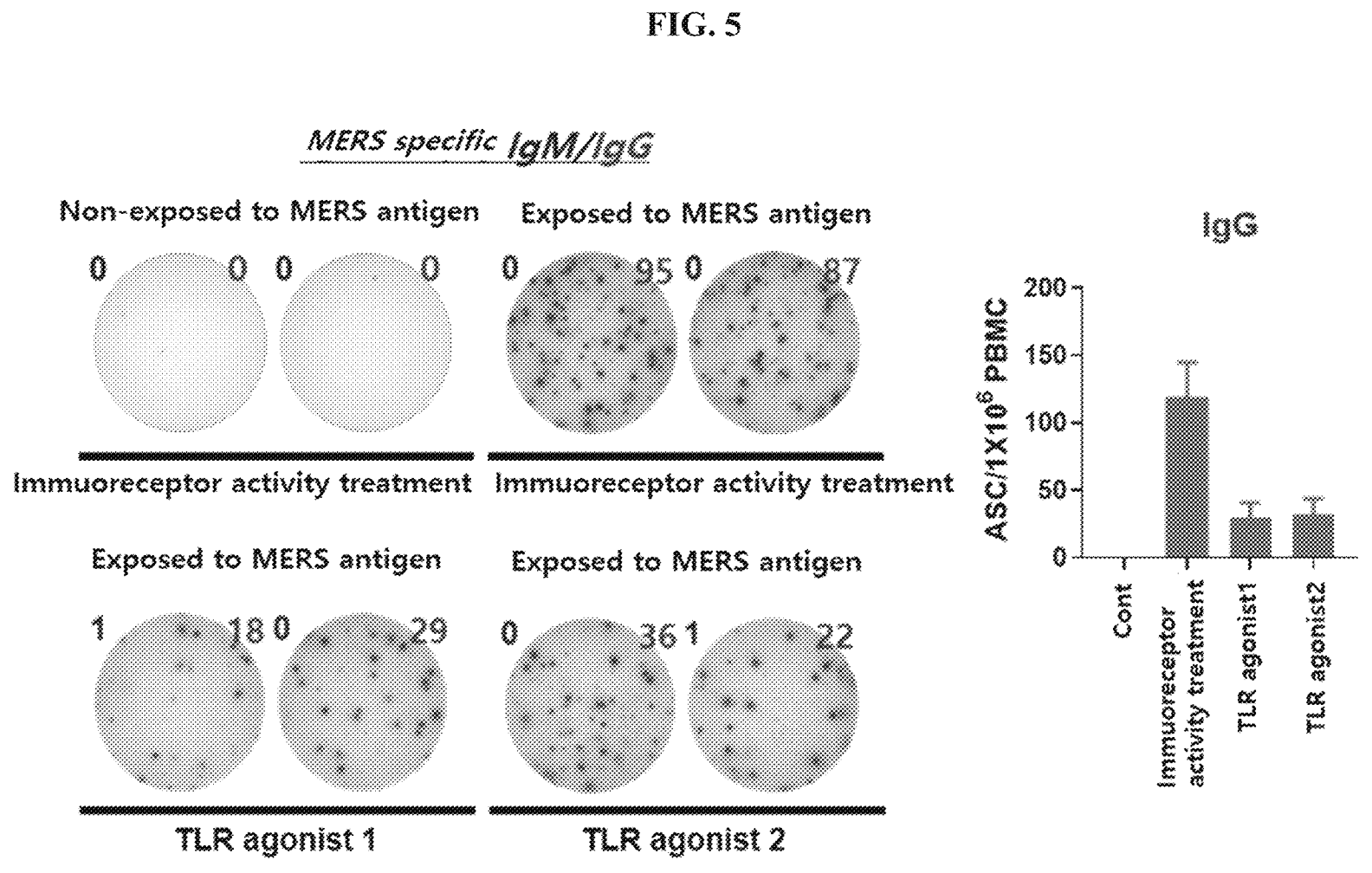

The result thereof was illustrated in FIG. 5.

As can be seen in FIG. 5, it could be confirmed that among monkey PBMCs in which the differentiation of memory B cells was induced according to the method of the present invention (immunoreceptor activity treated group), IgG (red number) and IgM (blue number) that specifically recognized the MERS antigen were accurately detected in PBMCs of two monkeys that had been exposed to the MERS virus, but were not detected in PBMCs of two monkeys that had not been exposed to the MERS virus. On the other hand, it could be confirmed that in the monkey PBMCs in which the differentiation of memory B cells was induced according to the method of the present invention, the secretion of an IgG-type antibody that specifically recognized the MERS antigen was significantly higher detected than a group treated with a polyclonal activator, TLR7/8 agonist (R848, TLR agonist1) or TLR9 agonist (CPG, TLR agonist 2).

In addition, in the same method as the method, the experiment was performed using PBMCs of monkeys that have been tertiary-inoculated with the Dengue virus antigen protein and adjuvant in the thigh muscles or monkeys infected with severe acute respiratory syndrome-corona virus (SARS-CoV-2). As a result, it could be confirmed that in monkey PBMCs that have been exposed to each viral antigen, IgG (red number) and IgM (blue number) that specifically recognized a Dengue virus antigen (a) or a COVID-19 virus antigen (b) were accurately detected, and in monkey PBMCs that have not been exposed to each viral antigen, the antibodies were not detected.

INDUSTRIAL APPLICABILITY

According to the method of the present invention, since only memory B cells present in a biological sample may be specifically differentiated, it is possible to very accurately and quickly analyze whether a subject providing the biological sample has a history of infection with pathogenic substances containing a specific antigen.

What is claimed is:

1. A method for detecting antigen-specific memory B cells in a subject that may have been infected with viruses or bacteria comprising the steps of:

(a) contacting a biological sample obtained from the subject with an anti-CD3 antibody or ligand, and an anti-CD28 antibody or ligand, wherein the biological sample comprises memory B cells and wherein the anti-CD3 antibody or ligand and the anti-CD28 antibody or ligand induce the differentiation of the memory B cells;

(b) contacting the biological sample of step (a) with an antigen; and (c) detecting an antibody that is secreted by the antigen-specific memory B cells in the biological sample and that specifically binds to the antigen of step (b) wherein the antigen is expressed by the viruses or bacteria which may have infected the subject.

2. The method of claim 1, further comprising:

removing CD8$^+$ T cells from the biological sample before contacting the biological sample obtained from the subject with the anti-CD3 antibody or ligand, and the anti-CD28 antibody or ligand in step (a).

3. The method of claim 1, wherein the antigen is at least one selected from the group consisting of a *Mycobacterium tuberculosis* antigen, an anthrax antigen, a Hepatitis A virus (HAV) antigen, a Hepatitis B virus (HBV) antigen, a Hepatitis C virus (HCV) antigen, a human immunodeficiency virus (HIV) antigen, an influenza virus antigen, a Herpes simplex virus (HSV) antigen, a *Haemophilus influenzae* type b (Hib) antigen, a *Neisseria meningitidis* antigen, a *Corynebacterium diphtheria* antigen, a *Bordetella pertussis* antigen, a *Clostridium tetani* antigen, a human papilloma virus (HPV) antigen, a Varicella virus antigen, an Enterococci antigen, a *Staphylococcus aureus* antigen, a *Klebsiella pneumonia* antigen, an *Acinetobacter baumannii*-antigent antigen, a *Pseudomonas aeruginosa* antigen, an *Enterobacter* antigen, a *Helicobacter pylori* antigen, a malaria antigen, a Dengue virus antigen, a Middle East Respiratory Syndrome (MERS) virus antigen, a Zika virus antigen, an Orientia tsutsugamushi antigen, a severe fever with thrombocytopenia syndrome Bunyavirus (SFTS Bunyavirus) antigen, a Japanese encephalitis virus antigen, a severe acute respiratory syndrome-corona virus (SARS-CoV) antigen, a severe acute respiratory syndrome-corona virus (SARS-CoV-2) antigen, an Ebola virus antigen, a hepatitis C virus antigen, a hepatitis B virus antigen, an acute respiratory syndrome virus antigen, a West Nile virus antigen, a vesicular stomatitis virus antigen, a Newcastle disease virus antigen, and a pneumococcal antigen.

4. The method of claim 1, wherein the detection of the antibody specifically binding to the antigen in step (c) is performed by at least one method selected from the group consisting of enzyme-linked immunospot (ELISPOT), enzyme-linked immunosorbent assay (ELISA), competitive ELISA, a magnetic bead-based assay, and immunochromatography.

5. The method of claim 1, further comprising:

determining that the subject has a history of infection with bacteria or viruses expressing the antigen when the antibody specifically binding to the antigen is detected in step (c).

6. A composition for specifically inducing differentiation of memory B cells using the method of claim 1 comprising an anti-CD3 antibody or ligand; and an anti-CD28 antibody or ligand.

7. A method for specifically inducing differentiation of memory B cells comprising:

contacting a biological sample obtained from a subject with an anti-CD3 antibody or ligand, and an anti-CD28 antibody or ligand, wherein the biological sample comprises the memory B cells in a subject that may have been infected with viruses or bacteria.

8. The method of claim 7, wherein the biological sample is selected from the group consisting of whole blood, peripheral blood mononuclear cells (PBMCs), and combinations thereof.

9. The method of claim 7, further comprising:

removing CD8$^+$ T cells from the biological sample before contacting the biological sample obtained from the subject with the anti-CD3 antibody or ligand, and the anti-CD28 antibody or ligand.

10. The method of claim 7, wherein the differentiation of the memory B cells is induced to secrete IgG and IgM.

* * * * *